(12) United States Patent
Hafliger et al.

(10) Patent No.: US 7,748,071 B2
(45) Date of Patent: *Jul. 6, 2010

(54) PERSONAL CARE ARTICLE WITH VIBRATING HEAD PART

(75) Inventors: Peter Hafliger, Triengen (CH); Franz Fischer, Triengen (CH); Gunther Elster, Gunzburg (DE)

(73) Assignee: Trisa Holding AG, Triengen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/318,844

(22) Filed: Jan. 9, 2009

(65) Prior Publication Data

US 2009/0126132 A1    May 21, 2009

Related U.S. Application Data

(60) Division of application No. 11/826,292, filed on Jul. 13, 2007, now Pat. No. 7,556,320, which is a continuation of application No. 11/245,027, filed on Oct. 7, 2005, now Pat. No. 7,261,851, which is a division of application No. 10/913,485, filed on Aug. 9, 2004, now Pat. No. 7,003,839, which is a division of application No. 10/093,699, filed on Mar. 11, 2002, now Pat. No. 6,802,097, which is a continuation of application No. PCT/CH00/00563, filed on Oct. 18, 2000.

(30) Foreign Application Priority Data

Oct. 19, 1999   (DE) ................................ 199 50 204
Nov. 3, 1999    (DE) ............................. 299 19 053 U

(51) Int. Cl.
*A46B 13/02*    (2006.01)
*A61C 17/22*    (2006.01)

(52) U.S. Cl. .......................................... 15/22.1; 15/28

(58) Field of Classification Search .................. 15/22.1, 15/23, 28
See application file for complete search history.

(56) References Cited

U.S. PATENT DOCUMENTS

| 3,346,748 | A | 10/1967 | McNair |
| 3,358,309 | A | 12/1967 | Richardson |
| 3,685,080 | A | 8/1972 | Hubner |
| 4,027,348 | A | 6/1977 | Flowers et al. |

(Continued)

FOREIGN PATENT DOCUMENTS

CN    2087500 U    10/1991

(Continued)

*Primary Examiner*—Randall Chin
(74) *Attorney, Agent, or Firm*—Oliff & Berridge, PLC

(57) ABSTRACT

An interdental treatment device, such as a toothbrush, includes a handle configured to accommodate an electric power source, a head carrying an interdental treatment tool, and a neck between the handle and the head. The head or neck includes a mechanical motorized vibratory device, including a drive which causes the head to vibrate. Electrical connections are operably connected to the mechanical vibratory device and the electric power source to power the mechanical vibratory device via the electrical connections. In various embodiments, a switch may be operably connected to at least one of the electrical connections to interrupt power from the power source to the mechanical motorized vibratory device. In various embodiments, a vibration-damping structure dampens vibration transmission from the head to the handle.

35 Claims, 2 Drawing Sheets

Fig. 3

U.S. PATENT DOCUMENTS

| | | |
|---|---|---|
| 5,033,150 A | 7/1991 | Gross et al. |
| 5,058,230 A | 10/1991 | Hodosh et al. |
| 5,071,348 A | 12/1991 | Woog |
| 5,123,841 A | 6/1992 | Millner |
| 5,138,733 A | 8/1992 | Bock |
| 5,165,131 A | 11/1992 | Staar |
| 5,259,083 A | 11/1993 | Stansbury |
| 5,267,579 A | 12/1993 | Bushberger |
| 5,353,460 A | 10/1994 | Bauman |
| 5,394,584 A | 3/1995 | Breitschmid |
| 5,435,033 A | 7/1995 | Millner |
| 5,471,695 A | 12/1995 | Aiyar |
| 5,511,270 A | 4/1996 | Eliacher et al. |
| 5,546,624 A | 8/1996 | Bock |
| 5,590,434 A | 1/1997 | Imai |
| 5,622,192 A | 4/1997 | Chiou |
| 5,706,541 A | 1/1998 | Gutelius et al. |
| 5,718,667 A | 2/1998 | Sugimoto et al. |
| 5,987,681 A | 11/1999 | Hahn et al. |
| 6,058,542 A | 5/2000 | Lo |
| 6,105,191 A | 8/2000 | Chen et al. |
| 6,464,920 B1 | 10/2002 | Kramer |
| 6,920,659 B2 | 7/2005 | Cacka et al. |
| 6,966,093 B2 | 11/2005 | Eliav et al. |
| 7,137,163 B2 | 11/2006 | Gatzemeyer et al. |
| 7,140,058 B2 | 11/2006 | Gatzemeyer et al. |
| 7,240,390 B2 | 7/2007 | Pfenniger et al. |
| 2002/0178519 A1 | 12/2002 | Zarlengo |
| 2003/0196283 A1 | 10/2003 | Eliav et al. |
| 2003/0226223 A1 | 12/2003 | Chan |
| 2005/0172493 A1 | 8/2005 | Fischer |
| 2006/0032512 A1 | 2/2006 | Kress et al. |

FOREIGN PATENT DOCUMENTS

| | | |
|---|---|---|
| EP | 704180 | 3/1996 |
| GB | 2 250 428 A | 10/1992 |
| JP | 3-222905 | 1/1991 |

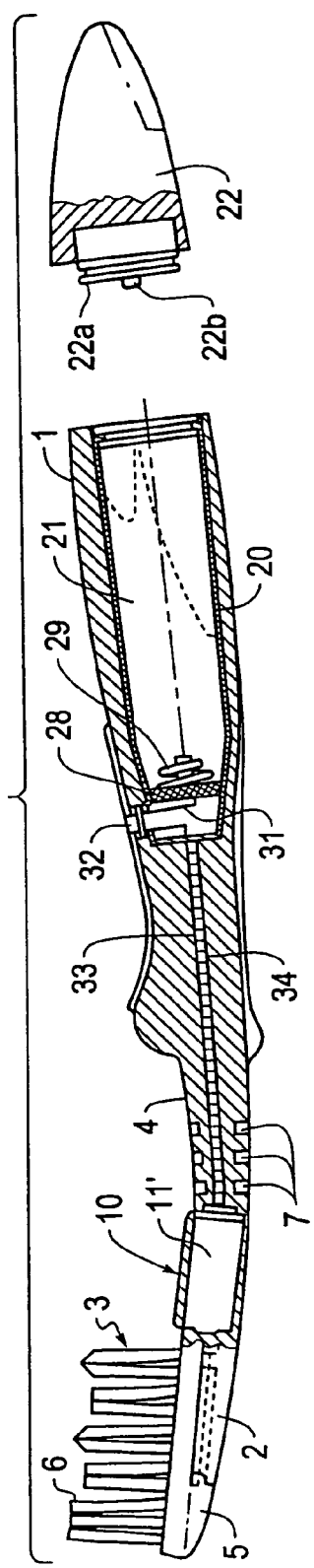
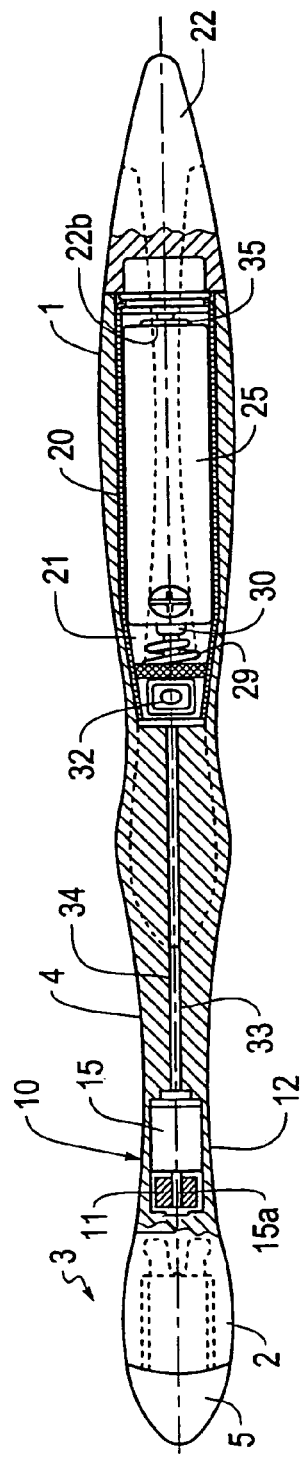
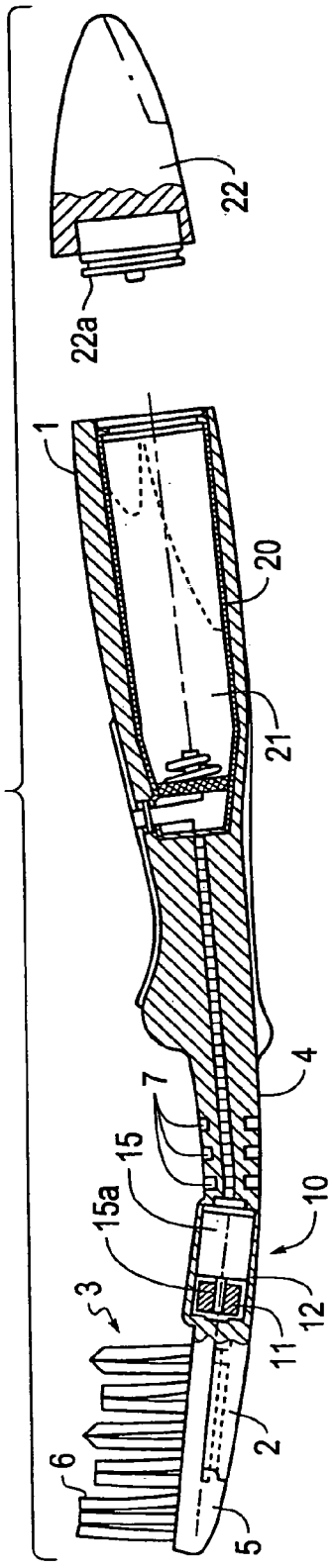
Fig. 1
Fig. 2
Fig. 3

PERSONAL CARE ARTICLE WITH VIBRATING HEAD PART

CROSS-REFERENCE TO RELATED APPLICATIONS

This is a Divisional of application Ser. No. 11/826,292 filed Jul. 13, 2007, now U.S. Pat. No. 7,556,320, which is a Continuation of application Ser. No. 11/245,027 filed Oct. 7, 2005, now U.S. Pat. No. 7,261,851, which is a Divisional of application Ser. No. 10/913,485 filed Aug. 9, 2004, now U.S. Pat. No. 7,003,839, which is a Divisional of application Ser. No. 10/093,699 filed Mar. 11, 2002, now U.S. Pat. No. 6,802,097, which is a Continuation of PCT/CH00/00563 filed Oct. 18, 2000, which claims priority from German Patent Application. No. 199 50 204.8 filed Oct. 19, 1999 and German Patent Application. No. 299 19 053.6 filed Nov. 3, 1999.

BACKGROUND OF THE INVENTION

1. Field of Invention

The invention relates to an interdental treatment device that includes an electrically powered vibrating head.

2. Description of Related Art

For teeth-cleaning purposes nowadays use is made either of conventional manual toothbrushes or of electric toothbrushes, in the case of which a movable brush head can be motor-driven from the handle. Electric toothbrushes usually achieve a more intensive cleaning action than the manual toothbrushes, but they have the disadvantage that they are relatively bulky and expensive and may damage the gums and subject the tooth enamel to pronounced abrasion.

SUMMARY OF THE INVENTION

An object of the present invention is to provide a cost-effective vibrating toothbrush which corresponds, in size, approximately to the conventional manual toothbrushes and nevertheless allows a better cleaning action than the latter.

This object is achieved according to the invention by a toothbrush including a vibrating head part, a mechanical vibratory device in at least one of the head and a neck, and a power supply, preferably in the handle.

Since a mechanical vibratory device which causes the head part to vibrate is accommodated in a front head part of the toothbrush, or in a neck-part region adjacent to the head part, the neck part connecting the head part to the handle, and is operatively connected to a power source, preferably accommodated in the handle, via electrical connections running in the neck part, vibration-damping means preferably being provided in order to prevent vibration transmission to the handle, this achieves the situation where the vibrations which effect the improved cleaning action are produced predominantly in the head part and can only be felt to a slight extent in the handle, as a result of which comfortable handling of the toothbrush is achieved. A further advantage of the toothbrush according to the invention is that there is no need for any mechanical drive means to be led through the flexible neck part to the vibratory device. It is merely the electrical connections, designed as wires, cables or electrically conductive plastic tracks, which run through the neck part.

Preferred developments of the toothbrush according to the invention form the subject matter of the dependent claims.

BRIEF DESCRIPTION OF THE DRAWINGS

The invention will now be explained in more detail with reference to the drawing, in which, purely schematically:

FIG. 1 shows a side view, partially in section, of a first exemplary embodiment of a toothbrush according to the invention and of a handle-closure part separated from one another (without a battery);

FIG. 2 shows a bottom view, partially in section, of a second exemplary embodiment of a toothbrush according to the invention in the assembled state;

FIG. 3 shows a side view, partially in section, of the toothbrush according to FIG. 2 and the closure part separated from one another (without a battery);

DETAILED DESCRIPTION OF PREFERRED EMBODIMENTS

Figure 4:
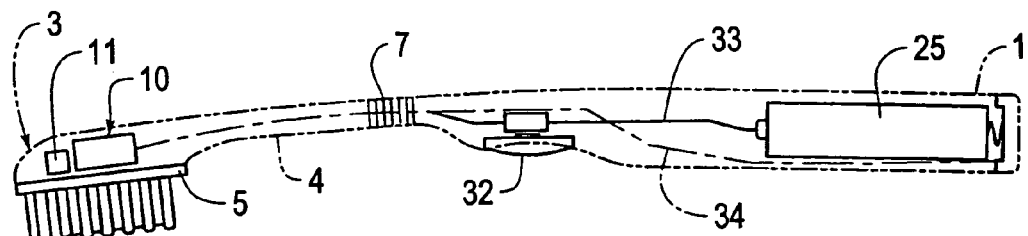
FIG. 4 shows a side view of a third exemplary embodiment of a toothbrush according to the invention in the assembled state.
Figure 5A:
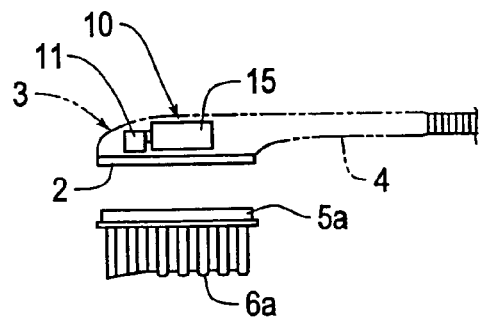
FIG. 5A shows a front part of the toothbrush according to FIG. 4 with different embodiments of exchangeable interdental treatment heads.
Figure 5B:
FIGS. 5B-D show different embodiments of exchangeable interdental treatment heads.
Figure 5C:
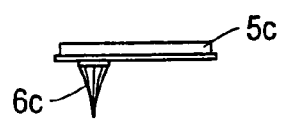
Figure 5D:
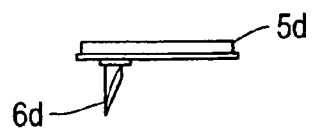

Both the toothbrush illustrated in FIG. 1 and that according to FIGS. 2 and 3 each have a handle 1, a front bristle-carrying head part 3 and a neck part 4, which connects the head part 3 to the handle 1. The bristles combined to form clusters of bristles 6 are anchored in a bristle carrier 5 and form a possibly profiled brushing surface with their free ends. In the embodiment illustrated, the bristle carrier 5 with the clusters of bristles 6 is positioned, in a manner which is known per se and thus is not described in any more detail, on a retaining part 2 of the head part 3 such that it can be exchanged.

The neck part 4 is provided with neck-part zones 7 which are made of an elastically relatively compliant material component and provide for, or additionally increase, the elasticity of the neck part 4, with the result that, during use of the interdental treatment device, the head part 3 can be forced back resiliently in the case of forces acting in the direction of the brushing surface. If appropriate, the neck-part zones 7 are designed as notches which extend over part of the neck circumference and are filled with elastically compliant material (e.g. with thermoplastic elastomer). Of course, it would also be quite conceivable for the form and number of neck-part zones to be different. It is also conceivable to have a flexible neck zone without using elastic material components, e.g. by providing constrictions or by way of a bellows.

Integrated in the front head part 3, or in that region of the neck part 4 which is adjacent to the head part 3, is a mechanical vibratory device 10, by means of which vibrations which effect or enhance the teeth-cleaning action may be imparted to the head part 3. The vibratory device 10 can be connected to an electric power source, accommodated in the handle 1, via electrical connections running in the neck part 4, as is described herein below. The already mentioned neck-part zones 7 made of an elastically compliant material act here as means which damp the vibration between the vibrating head part 3 and the handle 1, with the result that the vibratory action is produced, in particular, in the head part and is only transmitted to the handle 1 to a slight extent. This means that only slight vibrations can be felt in the handle 1 during the teeth-cleaning operation, and the toothbrush is thus comfortable to handle. Conversely, however, it is also advantageous that the vibration produced is not damped by the handle 1 and can act to full effect in the head part 3. Instead of the neck-part zones 7 consisting of elastically compliant material, however, other vibration-damping means would also be conceivable; it is not absolutely necessary to use an elastic material. The damping may also be achieved, using a basic material, by the neck part being configured in a particular form, for example by the presence of a bellows/accordion part, etc.

Accommodated in the handle 1 is a sheath or sleeve 20 which extends in the longitudinal direction of said handle and is made of electrically conductive material. Both the handle 1 and the sleeve 20 are open to the rear, this forming a cavity 21 which can be closed from the rear by a closure part 22 and into which it is possible to insert a battery 25, in the exemplary embodiment illustrated a commercially available, non-rechargeable cylindrical battery, with a defined power (e.g. 1.5 V) as the power source for the vibratory device 10. It would also be possible, however, for a button cell or for a rechargeable storage battery to be used as the power source.

A spring contact 29 for the positive pole 30 of the battery 25 (see FIG. 2) is fitted in the sleeve 20, on a transverse wall 28, and is connected to the vibratory device 10 via an electric line 31, a switch 32, which is installed in the sleeve 20 and can be actuated from the outside of the handle 1, and an electric line 33 running in the neck part 4. The electrical connection can be interrupted by means of the switch 32.

The closure part 22 is provided with a threaded stub 22a made of an electrically conductive material and can be screwed into the handle 1 and/or into the sleeve 20 by way of said threaded stub. The threaded stub 22a is provided with a contact surface 22b which, with the closure part 22 screwed in, comes into abutment against the negative pole 35 of the battery 25 inserted into the sleeve 20. The negative pole 35 is electrically connected to the vibratory device 10 via the threaded stub 22a, the sleeve 20 itself and a line 34, which connects the sleeve 20 to the vibratory device 10 and runs in the neck part 4.

Instead of being transmitted via the electrically conductive sleeve 20, it would also be possible for the power from the negative pole 35 to be transmitted in some other way, for example using wires or an electrically conductive plastic.

In the exemplary embodiment illustrated in FIG. 1, the vibratory device 10 comprises a vibratory element 11' which functions preferably in the manner of a vibratory armature, can be electrically connected directly to the power source via the lines 33, 34 and, with the power source connected, is made to vibrate.

In the case of the toothbrush variants illustrated in FIGS. 2 and 3, the vibratory device 10 comprises a vibratory element 11 in the form of an eccentric, which produces mechanical vibrations and can be rotated about an axis located in the longitudinal direction of the toothbrush, and also comprises a drive which is arranged directly adjacent and is designed as a micromotor 15. The vibratory element 11 is connected to the shaft 15a of the micromotor 15, which can be electrically connected to the power source via the lines 33, 34. The micromotor 15 and the eccentric may be accommodated as a structural unit in a housing 12.

Instead of an eccentric which can be driven in rotation, it would also be possible to have a vibratory element 11 which can be driven in a translatory manner.

It would be possible, in the case of the toothbrush according to the invention, to arrange the bristle-carrying head part 3 such that it can be moved in relation to the neck part 4 in order for the latter, in the case of vibrations produced by means of the vibratory device 10, to be made to move in relation to the rest of the toothbrush.

The electric lines 31, 33, 34 could also be realized by electricity-conducting plastic tracks.

The switch 32, which connects or interrupts the lines 31, 33, may also be, for example, a magnetic switch.

The preferred configuration of the switch 32, however, contains a pulse switch arranged on a printed circuit board as well as further electronic components which store the switching state.

It is also possible, however, for the electrical connection between the battery 25 and the vibratory element 11' (FIG. 1) or the drive 15 (FIGS. 2 and 3) to be produced or interrupted not by the switch 32, but by the closure part 22, which can be screwed into the handle 1 and/or into the sleeve 20 or connected to the same in a bayonet-like manner, being turned (i.e. the switch 32 is dispensed with in the case of such a configuration).

Instead of the rear closure part 22 being screwed to the handle 1, it would, of course, also be possible to have some other type of releasable connection (e.g. plug-in connection, bayonet connection, etc.) and a corresponding configuration of the contact part interacting with the negative pole 35.

It would also be possible for the closure part 22 to be in a form which is quite different to that illustrated in the drawing. For example, the closure part could be provided with a set-down surface or a foot part and thus serve as an element on which the toothbrush can be set down.

The toothbrush illustrated in FIG. 4 corresponds essentially to that according to FIGS. 2 and 3; the same parts, once again, have the same designations. According to FIG. 4, the vibratory device 10 is arranged directly in the front head part 3. In this exemplary embodiment, the sleeve 20 is dispensed with; the battery 25 is connected directly to the vibratory device 10 via the lines 33, 34. It is also the case with this device that use is preferably made of an exchangeable carrier 5 which can be positioned on a retaining part 2 of the head part 3, e.g. in the manner of a snap-in connection. The capacity for changing the bristle carrier 5 provided with the clusters of bristles 6 is particularly advantageous since the interdental treatment device provided with the vibratory device 10 can be used irrespective of the service life of the bristles, which is usually even shorter than the service life of the battery 25.

As can be seen from FIG. 5, it is possible, instead of the bristle carrier 5 or 5a, which forms part of a conventional brush head and is provided with respective clusters of bristles 6 or 6a, to position other, optionally different carriers or adapters 5b to 5d on the retaining part 2, these being provided with different interdental brushes 6b, 6c or interdental treatment parts 6d for effective cleaning of the spaces between the teeth. The interdental brush 6b may be designed, for example, as a helical brush made of coated wire with plastic filaments twisted in. The interdental brush 6c comprises bristles which, together, form a cluster tip. The treatment part 6d may be designed, for example, as a plastic element which has a tip and may preferably be provided with an abrasive coating for removing plaque and tartar from the spaces between the teeth. Of course, it would also be possible to use any other desired treatment heads.

It is also the case with the variant according to FIGS. 4 and 5 that the bristle carrier 5 could be configured such that a vibration-induced movement in relation to the retaining part 2 were possible.

For the introduction of the vibratory device 10, the connecting lines 33, 34 and further electronic components, it is possible for the toothbrush according to the invention, or the housing thereof, to be produced in two parts and for the two parts to be welded in a water-tight manner once the above-mentioned parts have been positioned therein.

It is also possible, however, for the toothbrush according to the invention to be produced by injection molding preferably involving two or more components. The abovementioned parts are advantageously positioned as a unit in an injection molding made of a first material component and then encapsulated in the second material component (or in the further material component) by injection molding. It is not necessary here for full encapsulation to take place. Certain parts may be exposed, as a result of which it is possible to achieve an esthetic effect.

It would also be possible, however, for the abovementioned electronic components to be inserted into a ready molded handle 1.

Since it is not only the vibratory element 11, 11' itself but also the drive, i.e. the micromotor 15, which are arranged in the front head part 3, or in the directly adjacent front region of the neck part 4, it is not necessary for any mechanical drive means to be led through the flexible neck part 4 in order to connect the micromotor to the vibratory element 11. It is only the electric lines 33, 34 (wires, cables or electrically conductive plastic tracks) which run through the neck part 4.

According to the invention, use is made of a mechanical vibratory device 10 which has a diameter of less than 15 mm, preferably less than 6 mm, and is less than 35 mm, preferably less than 20 mm, in length. This ensures that the toothbrush may be of ergonomic configuration and is easy to handle. The toothbrush according to the invention may correspond, in size, more or less to the conventional manual toothbrushes, which makes them more straightforward to handle in comparison with the commercially available, considerably larger electric toothbrushes, even though this toothbrush achieves a cleaning action which is comparable with that of the known electric toothbrushes, but is gentler than the latter. Moreover, the toothbrush according to the invention is straightforward and cost-effective to produce.

It is nevertheless also possible for the vibratory device according to the invention to be integrated in conventional electric toothbrushes.

What is claimed is:

1. In a personal care article, the improvement comprising:
   a handle configured to accommodate an electric power source;
   a bristle-carrying head;
   a neck between the handle and the head;
   a mechanical motorized vibratory device, including a drive which causes the head to vibrate, located in the neck; and
   electrical connections operably connected to the mechanical motorized vibratory device and operably connectable to the electric power source to power the mechanical vibratory device via the electrical connections.

2. The personal care article as recited in claim 1, wherein the mechanical motorized vibratory device has a vibratory element drivable by the drive, the drive being arranged directly adjacent to the vibratory element.

3. The personal care article as recited in claim 1, wherein the mechanical motorized vibratory device comprises an eccentric body rotatable about an axis of the drive.

4. The personal care article as recited in claim 1, wherein the mechanical motorized vibratory device has a vibrating element including a vibratory armature that forms the drive electrically connected to the power source to make the head vibrate.

5. The personal care article as recited in claim 1, wherein the mechanical motorized vibratory device has a vibratory element including a vibratory armature that forms the drive.

6. The personal care article as recited in claim 1, wherein the treatment head includes a helical brush made of wire with plastic filaments twisted in.

7. The personal care article as recited in claim 1, the treatment head comprising a plastic element with a tip.

8. The personal care article as recited in claim 1, wherein the electric power source is a button cell.

9. The personal care article as recited in claim 1, wherein the electric power source is a cylindrical battery.

10. The personal care article as recited in claim 1, wherein the neck includes at least one vibration-damping zone comprising an elastically compliant material.

11. The personal care article as recited in claim 1, wherein the neck includes notches that extend over part of the neck circumference.

12. The personal care article as recited in claim 1, wherein the notches are filled with elastically compliant material.

13. The personal care article as recited in claim 1, wherein the neck includes a flexible zone formed by constrictions or a bellows.

14. The personal care article as recited in claim 1, wherein the mechanical motorized vibratory device has a diameter of less than 6 mm.

15. The personal care article as recited in claim 1, further comprising a vibration-damping structure that dampens vibration transmission from the head to the handle.

16. The personal care article as recited in claim 1, wherein the handle includes a cavity, the power source is an exchangeable battery insertable into the cavity, the electrical connections are configured for electrical connection with the battery, and the cavity contains a sleeve made of electrically conductive material and which is open to the rear and can be closed from the rear by a cover.

17. In a personal care article, the improvement comprising:
   a handle configured to accommodate an electric power source;
   a bristle-carrying head;
   a neck between the handle and the head;
   a mechanical motorized vibratory device, including a drive which causes the head to vibrate, located in the neck and having an axis of rotation oriented in a substantially longitudinal direction of a portion of the personal care article in which the device is located; and
   electrical connections operably connected to the mechanical motorized vibratory device and operably connectable to the electric power source to power the mechanical motorized vibratory device via the electrical connections.

18. In a personal care article, the improvement comprising:
   a handle configured to accommodate an electric power source;
   a bristle-carrying treatment head;
   a neck between the handle and the treatment head;
   a mechanical motorized vibratory device, including a drive which causes the treatment head to vibrate, located in the neck and having an axis of rotation oriented in a substantially longitudinal direction of a portion of the personal care article in which the device is located; and
   electrical connections operably connected to the mechanical motorized vibratory device and operably connectable to the electric power source to power the mechanical motorized vibratory device via the electrical connections.

19. In a personal care article, the improvement comprising:
   an injection molded first material;
   an injection molded second material;

a handle configured to accommodate an electric power source;
a bristle-carrying head;
a neck between the handle and the head;
a mechanical motorized vibratory device, including a drive which causes the head to vibrate, located in at least one of the head and the neck; and
electrical connections operably connected to the mechanical motorized vibratory device and operably connectable to the electric power source to power the mechanical motorized vibratory device via the electrical connections,
wherein the mechanical motorized vibratory device includes mechanical and electrical components, wherein at least a portion of the mechanical and electrical components form a unit which is encapsulated within the injection molded first material and which is further at least partially encapsulated in the injection molded second material.

20. In a personal care article, the improvement comprising:
first and second article parts which are separately produced;
a handle configured to accommodate an electric power source;
a bristle-carrying head;
a neck between the handle and the head;
a mechanical motorized vibratory device, including a drive which causes the head to vibrate, located in the neck; and
electrical connections operably connected to the mechanical motorized vibratory device and operably connectable to the electric power source to power the mechanical motorized vibratory device via the electrical connections,
wherein the mechanical motorized vibratory device includes mechanical and electrical components, wherein at least a portion of the mechanical and electrical components form a unit which is received between the first and second separately produced personal care article parts that are connected to one another in a water-tight manner.

21. In a personal care article, the improvement comprising:
a handle configured to accommodate an electric power source;
a bristle-carrying head;
a neck between the handle and the head;
a mechanical motorized vibratory device, including a drive which causes the head to vibrate, located in at least one of the head and the neck and having an axis of rotation oriented in a substantially longitudinal direction of a portion of the personal care article in which the device is located; and
electrical connections operably connected to the mechanical motorized vibratory device and operably connectable to the electric power source to power the mechanical motorized vibratory device via the electrical connection,
wherein the mechanical motorized vibratory device has a diameter of less than 6 mm.

22. In a personal care article, the improvement comprising:
a handle configured to accommodate an electric power source;
a head comprising a helical brush;
a neck between the handle and the head;
a mechanical motorized vibratory device, including a drive which causes the head to vibrate, located in the neck and having an axis of rotation oriented in a substantially longitudinal direction of a portion of the personal care article in which the device is located; and
electrical connections operably connected to the mechanical motorized vibratory device and operably connectable to the electric power source to power the mechanical motorized vibratory device via the electrical connections.

23. The personal care article as recited in claim 22, wherein the helical brush is made of wire with plastic filaments twisted in.

24. The personal care article as recited in claim 22, wherein the treatment head includes a plastic element with a tip.

25. The personal care article as recited in claim 22, wherein the electric power source is a button cell.

26. The personal care article as recited in claim 22, wherein the electric power source is a cylindrical battery.

27. The personal care article as recited in claim 22, wherein the neck includes at least one vibration-damping zone comprising an elastically compliant material.

28. The personal care article as recited in claim 22, wherein the neck includes notches that extend over part of the neck circumference.

29. The personal care article as recited in claim 28, wherein the notches are filled with elastically compliant material.

30. The personal care article as recited in claim 22, wherein the neck includes a flexible zone formed by constrictions or a bellows.

31. The personal care article as recited in claim 22, wherein the mechanical motorized vibratory device has a diameter of less than 6 mm.

32. The personal care article as recited in claim 22, further comprising a vibration-damping structure that dampens vibration transmission from the head to the handle.

33. The personal care article as recited in claim 22, wherein the mechanical motorized vibratory device has a vibratory element drivable by the drive, the drive being arranged directly adjacent to the vibratory element.

34. The personal care article as recited in claim 22, wherein the mechanical motorized vibratory device comprises an eccentric body that can be rotated about an axis of the drive.

35. The personal care article as recited in claim 22, wherein the handle includes a cavity, the power source is an exchangeable battery insertable into the cavity, the electrical connections are configured for electrical connection with the battery, and the cavity contains a sleeve made of electrically conductive material and which is open to the rear and can be closed from the rear by a cover.

* * * * *